United States Patent
Moulin et al.

(10) Patent No.: US 8,992,083 B2
(45) Date of Patent: Mar. 31, 2015

(54) SYSTEM AND METHOD OF LOCATING AN X-RAY IMAGING APPARATUS AND CORRESPONDING X-RAY IMAGING APPARATUS

(75) Inventors: Romain Moulin, Paris (FR); Carlos Martinez Ferreira, Paris (FR)

(73) Assignee: General Electric Company, Schenectady, NY (US)

( * ) Notice: Subject to any disclaimer, the term of this patent is extended or adjusted under 35 U.S.C. 154(b) by 438 days.

(21) Appl. No.: 13/548,809

(22) Filed: Jul. 13, 2012

(65) Prior Publication Data

US 2013/0243166 A1    Sep. 19, 2013

(30) Foreign Application Priority Data

Jul. 13, 2011   (EP) ..................................... 11305925

(51) Int. Cl.
   *H05G 1/02*     (2006.01)
   *G01B 7/30*     (2006.01)
   *A61B 6/00*     (2006.01)
   *A61B 19/00*    (2006.01)

(52) U.S. Cl.
   CPC ............... *G01B 7/30* (2013.01); *A61B 6/4405* (2013.01); *A61B 6/4429* (2013.01); *A61B 6/4441* (2013.01); *A61B 6/4458* (2013.01); *A61B 6/4476* (2013.01); *A61B 6/547* (2013.01); *A61B 6/56* (2013.01); *H05G 1/02* (2013.01); *A61B 2019/5238* (2013.01); *A61B 6/548* (2013.01)
   USPC ............................................ 378/207; 378/62

(58) Field of Classification Search
   USPC ............................................ 378/207, 15, 62
   See application file for complete search history.

(56) References Cited

U.S. PATENT DOCUMENTS

| 4,119,212 A | 10/1978 | Flemming |
| 5,657,498 A | 8/1997 | Hum |
| 6,435,715 B1 | 8/2002 | Betz et al. |
| 2004/0013239 A1* | 1/2004 | Gregerson et al. ............ 378/197 |
| 2005/0070779 A1* | 3/2005 | Singh B et al. ............... 600/407 |
| 2006/0008046 A1* | 1/2006 | Ruhrnschopf .................... 378/7 |
| 2006/0107542 A1 | 5/2006 | Song et al. |
| 2008/0013690 A1 | 1/2008 | Lurz et al. |
| 2010/0329426 A1* | 12/2010 | Oda et al. ..................... 378/98.2 |

FOREIGN PATENT DOCUMENTS

| DE | 10215987 A1 | 11/2003 |
| FR | 2945724 A1 | 11/2010 |
| JP | 2140149 A | 5/1990 |

OTHER PUBLICATIONS

EP Search Report dated Nov. 16, 2011 which was issued in connection with the EP Patent Application No. 11305925.7 which was filed Jul. 13, 2011.

* cited by examiner

*Primary Examiner* — Kiet T Nguyen
(74) *Attorney, Agent, or Firm* — GE Global Patent Operation; Mark A. Vivenzio

(57) ABSTRACT

A system for determining the position of an X-ray imaging apparatus mounted on an automatic mobile device is provided. The system comprises at least one mechanical link jointed to a reference point and to the X-ray imaging apparatus, and at least one measuring device configured to measure a variation of rotation angles of the at least one mechanical link relative to the reference point and to the X-ray imaging apparatus when moved.

10 Claims, 4 Drawing Sheets $x_{AGV} = L.\cos(\alpha_1) + L.\cos(\alpha_1 + \alpha_2)$ $y_{AGV} = L.\sin(\alpha_1) + L.\sin(\alpha_1 + \alpha_2)$ $\theta_{AGV} = \alpha_1 + \alpha_2 + \alpha_3$ X, Y accuracy in mm Angle accuracy in °

SYSTEM AND METHOD OF LOCATING AN X-RAY IMAGING APPARATUS AND CORRESPONDING X-RAY IMAGING APPARATUS

CROSS-REFERENCE TO RELATED APPLICATIONS

This application claims foreign priority benefits under 35 U.S.C.§119 to European Patent Application No. EP11305925.7, filed Jul. 13, 2011, which is hereby incorporated by reference in its entirety as part of the present disclosure.

BACKGROUND OF THE INVENTION

1. Field of the Invention

Embodiments of the present invention relate, in general, to medical imaging systems and, notably, to X-ray apparatuses used in the field of medical imaging. More specifically, the subject matter of the invention relates generally to X-ray imaging apparatuses that are mounted on a mobile device.

2. Description of the Related Art

X-ray apparatuses conventionally comprise an imaging assembly including an X-ray tube and an X-ray detector placed opposite the X-ray tube in a direction of emission of the X-rays. The tube and the detector are usually placed on two mutually opposite ends of an arm, so that the X-rays emitted by the tube can be incidental to and detected by the detector.

Such apparatuses are used for angiographic examinations with a diagnostic or an interventional aim.

During these examinations, it is necessary to produce radiographs of a region of interest in the body of a patient irradiated by X-rays. For this purpose, after the patient has been laid out on an examination table, the X-ray tube and the detector are brought to face the region to be radiographed and to be centred around the region of interest.

In the prior art, several types of X-ray apparatuses are known to produce radiographs.

First, X-ray apparatuses are known that are fixed to the ground, and in which the arm supporting the X-ray tube and the detector comprises several degrees of freedom, making it possible to position the X-ray beam facing the region of interest.

This type of apparatus however has a major drawback, relating to the fact that the radiography requirement is necessary only at the beginning and at the end of the intervention.

Meanwhile, the patient access should take precedence. However, the apparatus cannot be removed from the examination table when it is not used, such that, in particular, the transfer and installation of the patient on the examination table are altered by the presence of this cumbersome system.

Besides, conventional mobile X-ray imaging systems may be mounted on a carriage that can be moved manually and that contains a certain number of batteries used to supply the X-ray tube with power.

This type of apparatus is not suitable for angiographic examination because the necessary power delivered by the X-ray tube is no longer sufficient to obtain adequate image quality and, in particular, contrast.

Moreover, this type of mobile X-ray apparatus does not allow complex angulations because the diameter of the arm supporting the tube and the detector is not large enough.

Similarly, these mobile X-ray apparatuses do not achieve sufficient rotation speeds to allow good quality, three-dimensional image reconstructions. Finally, even though the weight of such an apparatus is half as much as that of an X-ray apparatus designed for angiography, it remains very difficult to move because of its relatively large dimensions and its weight, which can be up to 300 kg.

Moreover, X-ray apparatuses for angiography are known that are suspended to the ceiling and can be moved on guide rails, via a mobile carriage, for example with the aid of an electric motor.

This type of apparatus also has several drawbacks.

Firstly, many systems are already attached to the ceiling around the examination table, thus already cluttering the space around the patient, and making it difficult to install guide rails.

Secondly, mounting an X-ray apparatus on the ceiling considerably increases the risk of opportunistic contamination of the patient. Specifically, because of the difficulty of cleaning the rails, particles are likely to fall and contaminate the patient when the apparatus is sliding in the rails.

Moreover, in certain operating rooms, a sterile laminar flow is generated above the patient. In this case, the flow is likely to blow particles present on the rails, which can then enter the laminar flow and reach the patient.

There is therefore a need for a mobile imaging system that can be readily and automatically located in an operatic room and, notably, relative to an examination table.

Reference can be made to document FR 2 945 724 that discloses an X-ray imaging apparatus mounted on an automatic mobile device, which is capable of being moved automatically, either in a stand-alone manner, or under the control of a control console that can be operated by an operator. The X-ray apparatus is provided with a navigation system that can compute a trajectory for the imaging apparatus relative to a predefined trajectory.

However, it is necessary to determine the current position of the X-ray imaging apparatus to compute the trajectory and correct the computed trajectory relative to the predefined trajectory.

The current position can be determined either using optical readers operable to read or decode barcodes representative of a two-dimensional coordinates of their position in the environment, and to decode the information contained in the barcodes.

In another embodiment, the navigation system can be in communication with a GPS or global positioning system, operable to compute the position of the X-ray apparatus.

In a further example, the navigation system is operable to track the position of reflectors or detectors located in the operating room using a laser beam emitter and to compute the current position of the X-ray imaging apparatus from the duration between the incident laser beam and the reflected laser beam.

It has been found that such a navigation system is quite expensive and can be sensitive to disruptions from the environment interaction. In particular, the laser might be subject to booms, wall reflections or may be disrupted by outside light.

In the light of the foregoing, the object on the invention is to alleviate these drawbacks and to determine the position of an X-ray imaging apparatus without any interactions with the environment.

BRIEF DESCRIPTION OF THE INVENTION

According to an embodiment of the present invention, a system for determining the position of an X-ray imaging apparatus mounted on an automatic mobile device is provided. The system comprises at least one mechanical link jointed to a reference point and to the apparatus and at least one measuring device configured to measure a variation of rotation angles of the link relative to the reference point and to the apparatus when moved.

According to another embodiment of the present invention, an X-ray imaging apparatus is provided. The X-ray imaging apparatus comprises an imaging assembly mounted on an automatic mobile device; and a system for determining the position of the X-ray imaging apparatus, the system comprising at least one mechanical link jointed to a reference point and to the apparatus and at least one measuring device configured to measure a variation of rotation angles of the link relative to the reference point and to the apparatus when moved.

According to a further embodiment of the present invention a method of locating an X-ray imaging apparatus mounted on an automatic mobile device is provided. The method comprises measuring a variation of rotation angles of a mechanical link jointed to a reference point and to the X-ray imaging apparatus, the rotation angles being measured relative to the reference point and to the apparatus when moved and computing the coordinates of the apparatus from the measured angles and the length of the link.

BRIEF DESCRIPTION OF THE DRAWINGS

Other objects, features and advantages of the invention will appear on reading the following description given only as a non-limiting example and made with reference to the appended drawings in which.

DETAILED DESCRIPTION OF THE INVENTION

Figure 1:
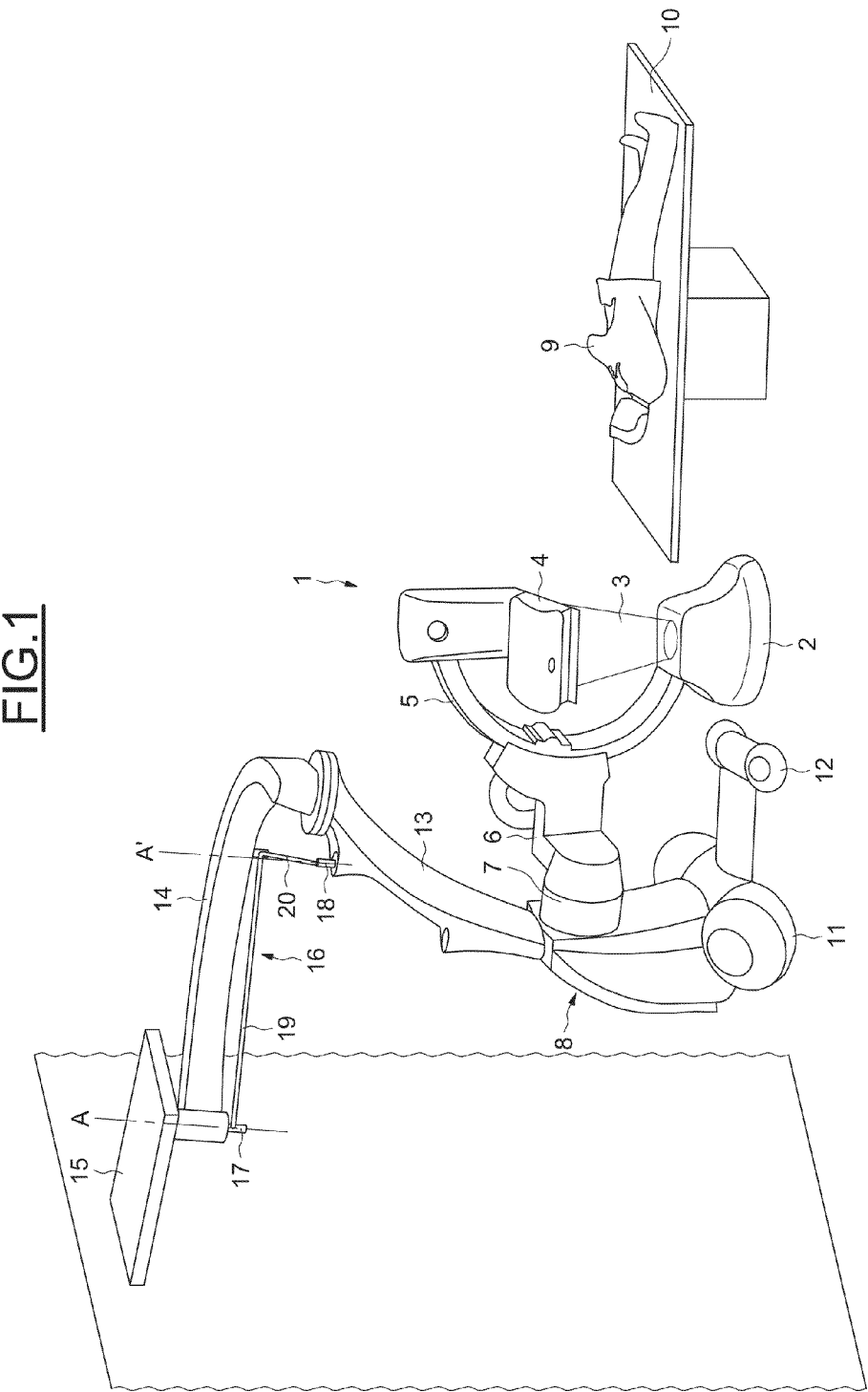
FIG. 1 is a schematic view of an X-ray apparatus according to an embodiment of the invention.

Reference is first made to FIG. 1, illustrating a perspective view of an X-ray imaging apparatus 1 for three-dimensional (3D) medical imaging according to one exemplary, but non-limited, application of the invention.

This imaging apparatus 1 is in particular intended to perform image acquisition of an object to be studied, for example a part of a patient body.

As can be seen, this apparatus 1 essentially comprises an imaging assembly having an X-ray tube 2, capable of emitting a beam 3 of X-rays in an emission direction, and an X-ray detector 4 placed at the two mutually opposed ends of an arm 5 in instance in the form of an arch, so that the X-rays emitted by the tube 2 are incident on the detector 4.

The arm 5 is mounted so as to slide on a second arm 6 mounted rotatingly on a fixed support 7, itself mounted on a base assembly having an automatic mobile device 8 operable to move across the floor of an operating or examination room.

Therefore, the support 7, the rotating arm 6 and the arm 5 are all three articulated relative to one another so that the imaging assembly can move in three dimensions and thus produce images of an organ to be examined from various angles of incidence.

During a radiography, the tube 2 and the detector 4 are brought to face an area of interest in the body 9 of a patient laid out on an examination table 10 so that, when the region of interest is interposed between the X-ray tube 2 and the detector 4, it is irradiated by the X-rays and the detector 4 produces data representative of characteristics of the interposed region of interest.

As can be seen, the mobile device 8 comprises, in the exemplary embodiment shown, a rolling system comprising two lateral driving and steering wheels 11 placed at the rear, and two free front wheels 12, the driving wheels being associated with driving means comprising a steering motor coupled to a driving motor.

The base assembly can thus be a robotised programmable device and may be associated with a navigation system operable to compute a trajectory or path for the X-ray imaging apparatus relative to predefined trajectories.

The navigation system, that can be embedded either within the X-ray apparatus or within a remote control console, is also operable to compute a current position of the apparatus, in order to allow the apparatus 1 to be located precisely in the operating room and, notably, relative to the examination table 10.

Therefore, according to programming phases or under the control of the control console that can be operated by an operator, the X-ray apparatus is capable of being moved automatically in the operating room.

This is in particular the case, notably, during the positioning of the X-ray apparatus facing the examination table, in order to place the tube 2 and the detector 4 facing a region of interest to be radiographed or during the movement of the X-ray apparatus to an out-of-the-way waiting position when it is no longer in use.

For example, the navigation system can compute the current position of the X-ray apparatus 1, and in particular the position of the imaging assembly to generate signals to the mobile device 8 to steer the base assembly relative to the optimal or pre-programmed trajectory or path.

It can also be seen in FIG. 1, that the apparatus 1 is provided with an arm 13 erected for example from the support 7, and in which are located a set of connection elements Such connection elements may comprise notably a set of power and electrical connection cables dedicated to supply the apparatus with electric power, of ducts in which a cooling fluid circulates, for example water, and of data transmission channels, for example of the optical fibre type.

This set of connection elements are in this instance connected to a remote cabinet, situated in a remote equipment room.

The connection elements are placed in a supporting device 14 consisting, for example, in a chain of articulated links capable of confining the bundle of connection elements in a horizontal plane, and situated in the vicinity of the ceiling of the operating or examination room.

The supporting device 14 is connected, at one end, to the erected arm 13 and, at the opposite end, to a fixed support element 15, for example mounted on the wall of the operating room, in the vicinity of the ceiling, as shown.

For example, the chain 14 may be provided with a set of chain links each articulated with each other, so that when the base assembly and, consequently, the X-ray imaging apparatus 1 is moved across the floor, the deformation of the chain occurs.

It should be appreciated that the mutually opposite ends of the chain 14 are jointed to the support element 15 and to the arm 13, respectively.

In order to determine its current position, the X-ray imaging apparatus is provided with a localization system associated with the navigation system.

Figure 2:
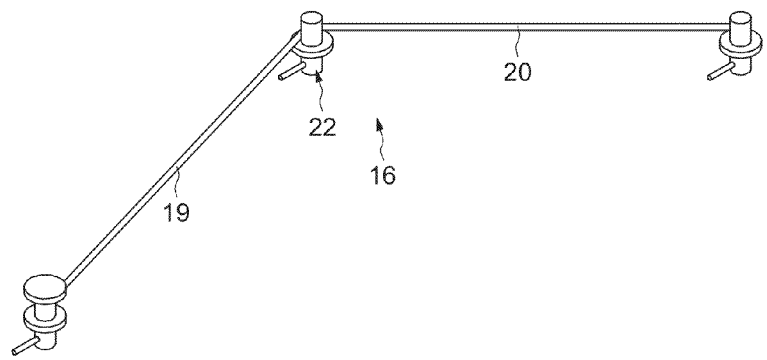
FIG. 2 illustrates an embodiment of a system for determining the position of the X-ray imaging apparatus of FIG. 1.

As shown in FIGS. 1 and 2, the localization system comprises at least one mechanical link 16 lying beneath the chain 14 and having two mutually opposite ends 17 and 18 jointed to the support element 15 and to the erected arm 13.

In the exemplary embodiment of FIGS. 1 and 2, the link 16 comprises two rectilinear beams 19 and 20 jointed to each other.

Each beam has a first end jointed to a corresponding end of the other beam, and an opposite end, namely the ends denoted by reference numerals 17 and 18 jointed to the support element 15, and to the erected arm 13, respectively.

In other words, the link 16 is mounted on the support element 15 and on the erected arm 13 by means of two pivot axes A and A' such that when the X-ray imaging apparatus is moved by the mobile device across the floor, a shift of the angle of rotation of the first beam 19 around the pivot axis A as well as a shift of the angle of rotation of the apparatus around the pivot axis A' occur. In addition, the angle formed by the beams 19 and 20 varies according to the movement of the X-ray apparatus 1.

The localization system is further provided with calculating means including a computer associated with a program memory, operable to monitor a shift of rotation angles of the link 16 relative to the support element 15 and to the erected arm 13 as well as a variation of the rotation angle between the arms 19 and 20, and to derive therefrom the actual position of the X-ray apparatus relative to a reference point formed in this instance by the pivot axis A.

Figure 3:
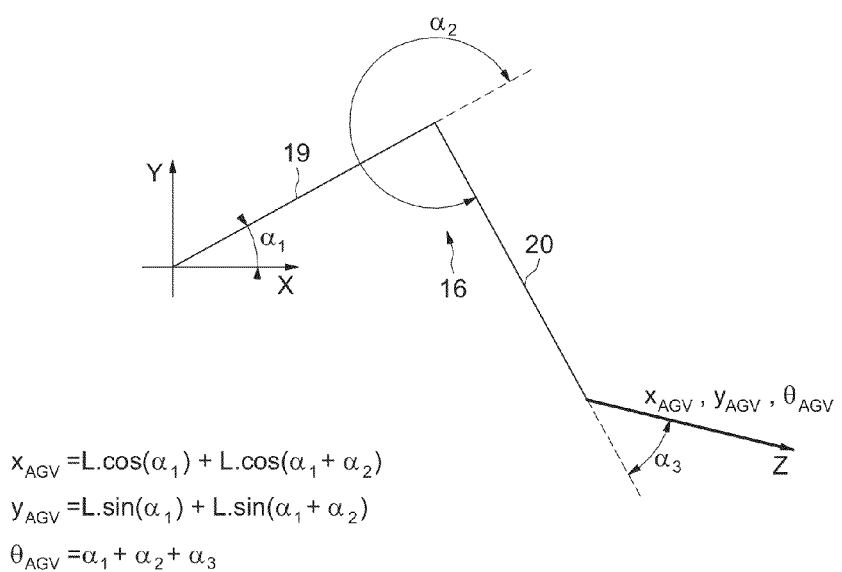
FIG. 3 is a schematic view of the link of FIG. 2, showing the calculation functions used to compute the position of the X-ray imaging apparatus.

As shown on FIGS. 2 and 3, each end of the beams is provided with an angle measurement encoder, such as 22, in order to measure the angle $\alpha 1$ between the direction X of the support element 15 and the first beam 19, the angle $\alpha 2$ between the first and second beams 19 and 20 and the angle $\alpha 3$ between the second beam 20 and the general axis Z of the X-ray apparatus.

Such angle measurement encoders are well known in the state of the art and will not be further disclosed.

Referring now to FIG. 3, the calculating means compute the actual location and orientation of the X-ray apparatus system using the measured values of the angles $\alpha 1$, $\alpha 2$ and $\alpha 3$. In particular, the calculating means calculate the coordinate X and Y of the apparatus within a Cartesian coordinate system and the orientation $\theta$ of the X-ray apparatus relative to the general axis of the support element 15 using in the following equations:

$$X = L \cos \alpha 1 + L \cos(\alpha 1 + \alpha 2)$$

$$Y = L \sin \alpha 1 + L \sin(\alpha 1 + \alpha 2)$$

$$\theta = \alpha 1 + \alpha 2 + \alpha 3$$

in which:
X and Y denote the coordinates of the apparatus within a Cartesian coordinate system; $\theta$ denotes the orientation of the X-ray apparatus; and L denotes the length of each beam.

It should be appreciated that each beam has sufficient rigidity to provide a sufficient accuracy on the thus computed position of the X-ray imaging apparatus.

For example, each beam is realized in the form of a tube made of carbon fibres.

It should also be appreciated that in the above mentioned embodiment, the localization system, having two beams provided with three angle encoders, is able to compute the position of the X-ray imaging apparatus without any interaction with the environment in which the apparatus is located, and without increasing the bulk dimensions of the apparatus.

However, it will be noted that the invention is not limited to the embodiment described.

As a matter of fact, in the embodiment described above, the link jointed to the reference point and to the apparatus comprises two beams.

It should be understood that such a link may be provided with a different number of beams, and may comprise at least one beam.

Preferably, the link may comprise at least two beams, for example two beams as disclosed above, or three or more beams.

In addition, the link may comprise a wire link, the wire of which being linked to the erected arm 13, and wound on a drum mounted on the support element 15. The wire link may, for example, comprise a spring-loading device and be associated with an encoder operable to count the number of revolutions of the wire around the drum, and a further encoder operable to detect the angular orientation of the drum relative to the support element 15.

Figure 4:
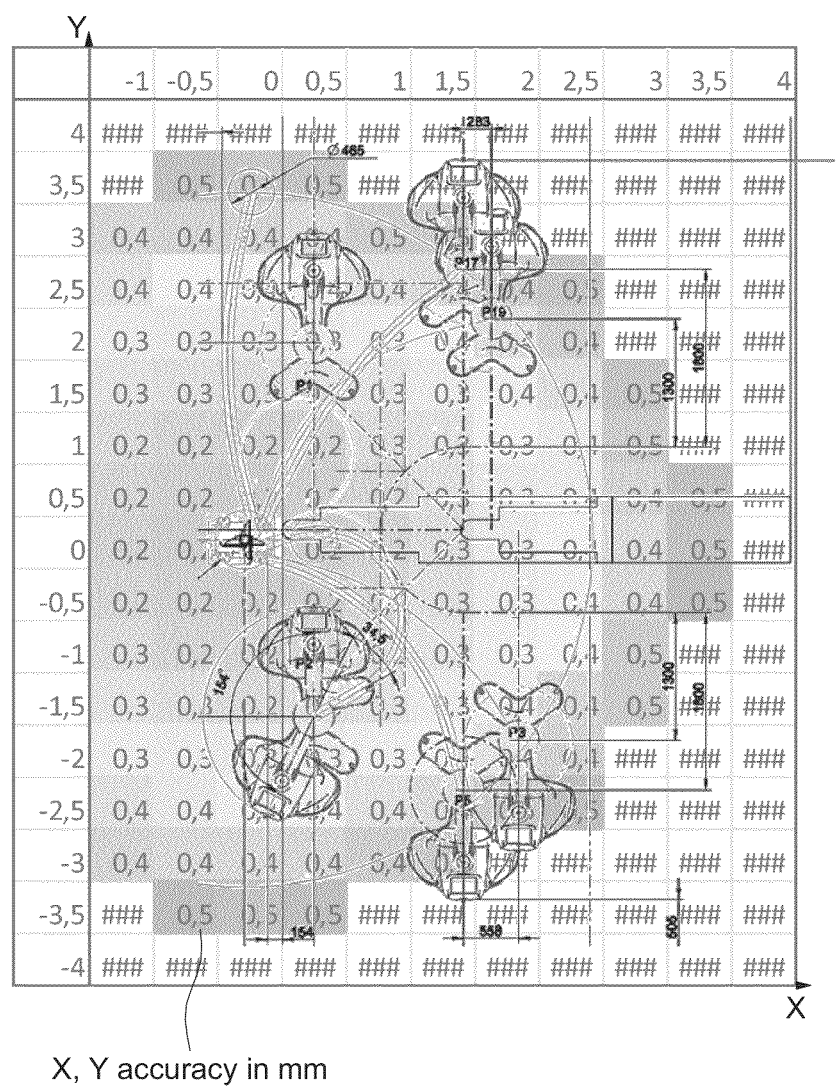
FIGS. 4 and 5 are diagrams showing the accuracy of the position calculation.
Figure 5:
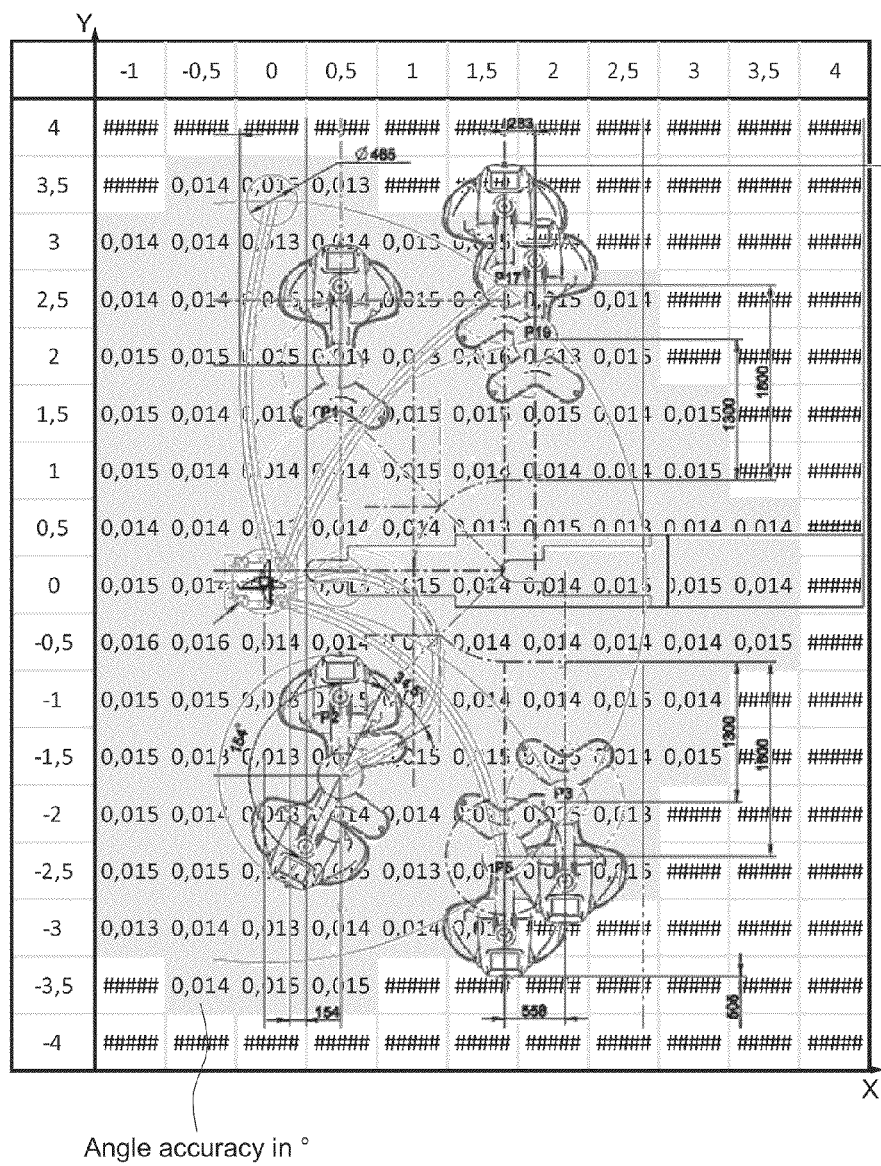

Referring finally to FIGS. 4 and 5, it will be appreciated that the localization system as disclosed above is capable of determining the position of the X-ray imaging apparatus with an accuracy of about 0.5 mm around the examination table 10.

Besides, the angle of the X-ray imaging apparatus relating to a predefined orientation, for example the general orientation of the support element 15, can be determined with an accuracy of about 0.02°.

It will be understood that such an accuracy may be obtained by virtue of an X-ray imagining apparatus mounted on an automatic mobile device and comprising at least one mechanical link jointed to a reference point and to the apparatus and a set of angle encoders for measuring a variation of rotation angles of said link relating to the reference point and to the apparatus when moved.

Embodiments of the present invention make it possible to determine the position of an X-ray imaging apparatus only from the variation of the lay out of the link between the reference point, for example a stationary location within the operating room, and the X-ray apparatus.

According to an embodiment of the present invention, the link may comprise at least two beams jointed to each other, and having opposite ends jointed to said reference point and to the apparatus, respectively.

The system may thus comprise a first measuring means mounted on a first joint linking the first beam to the reference point, a second measuring means mounted on a second joint linking the two beams, and a third measuring means mounted on a third joint linking the second beam to the apparatus.

In an embodiment, at least one of the measuring means comprises an encoder, such as an angle measurement encoder.

In a further embodiment, the system further comprises calculating means for calculating the position of the X-ray apparatus from the length of the link and the measured angle variation.

What is claimed is:

1. A system for determining the position of an X-ray imaging apparatus mounted on an automatic mobile device, the system comprising:
   at least one mechanical link jointed to a reference point and to the X-ray imaging apparatus; and
   at least one measuring device configured to measure a variation of rotation angles of the at least one mechanical link relative to the reference point and to the X-ray imaging apparatus when moved.

2. A system according to claim 1, wherein the at least one mechanical link comprises at least two beams jointed to each other.

3. The system according to claim 2, wherein the at least two beams comprise a first beam and a second beam jointed to each other, and wherein an end of the first beam is jointed to the reference point and an end of the second beam is jointed to the X-ray imaging apparatus.

4. The system according to claim 3, wherein the at least one measuring device comprises a first measuring device mounted on a first joint linking the first beam to the reference point, a second measuring device mounted on a second joint linking the first beam and the second beam, and a third measuring device mounted on a third joint linking the second beam to the X-ray imaging apparatus.

5. The System of claim 4, wherein at least one of the first, second and third measuring devices comprises an encoder.

6. The system according to claim 1, wherein the at least one measuring device comprises an angle measurement encoder.

7. The system according to claim 1, further comprising a calculator configured to calculate the position of the X-ray imaging apparatus from the length of the at least one mechanical link and the measured variation of rotation angles.

8. The system according to claim 7, wherein the coordinates and orientation of the X-ray imaging apparatus are calculated from the following equations:

$$X = L \cos \alpha_1 + L \cos(\alpha_1 + \alpha_2)$$

$$Y = L \sin \alpha_1 + L \sin(\alpha_1 + \alpha_2)$$

$$\theta = \alpha_1 + \alpha_2 + \alpha_3$$

in which:
X and Y denote the coordinates of the X-ray imaging apparatus within a Cartesian coordinate system; and
$\theta$ denotes the orientation of the X-ray imaging apparatus.

9. An X-ray imaging apparatus, comprising:
an imaging assembly mounted on an automatic mobile device; and
a system for determining the position of the X-ray imaging apparatus, the system comprising at least one mechanical link jointed to a reference point and to the X-ray imaging apparatus and at least one measuring device configured to measure a variation of rotation angles of the at least one mechanical link relative to the reference point and to the X-ray imaging apparatus when moved.

10. A method for locating an X-ray imaging apparatus mounted on an automatic mobile device, comprising:
measuring a variation of rotation angles of a mechanical link jointed to a reference point and to the X-ray imaging apparatus, the rotation angles being measured relative to the reference point and to the X-ray imaging apparatus when moved; and
computing the coordinates of the X-ray imaging apparatus from the measured angles and the length of the link.

* * * * *